United States Patent
Pimentel et al.

(10) Patent No.: US 10,527,621 B2
(45) Date of Patent: *Jan. 7, 2020

(54) ANTIBODY TO CYTOLETHAL DISTENDING TOXIN OF CAMPYLOBACTER JEJUNI

(71) Applicant: Cedars-Sinai Medical Center, Los Angeles, CA (US)

(72) Inventors: Mark Pimentel, Los Angeles, CA (US); Christopher Chang, Albuquerque, NM (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/185,955

(22) Filed: Nov. 9, 2018

(65) Prior Publication Data

US 2019/0178890 A1    Jun. 13, 2019

Related U.S. Application Data

(63) Continuation of application No. 15/855,792, filed on Dec. 27, 2017, now Pat. No. 10,151,752, which is a continuation of application No. 14/793,523, filed on Jul. 7, 2015, now Pat. No. 9,869,676, which is a continuation of application No. 13/148,252, filed as application No. PCT/US2010/023911 on Feb. 11, 2010, now Pat. No. 9,110,081.

(60) Provisional application No. 61/151,779, filed on Feb. 11, 2009, provisional application No. 61/286,250, filed on Dec. 14, 2009.

(51) Int. Cl.
| | | |
|---|---|---|
| G01N 33/573 | (2006.01) | |
| G01N 33/68 | (2006.01) | |
| C07K 16/12 | (2006.01) | |
| A61K 39/02 | (2006.01) | |
| A61K 39/00 | (2006.01) | |

(52) U.S. Cl.
CPC ......... G01N 33/573 (2013.01); A61K 39/02 (2013.01); A61K 39/105 (2013.01); C07K 16/12 (2013.01); C07K 16/121 (2013.01); G01N 33/6893 (2013.01); A61K 2039/522 (2013.01); C07K 2317/34 (2013.01); G01N 2333/24 (2013.01); G01N 2333/25 (2013.01); G01N 2333/922 (2013.01); G01N 2800/065 (2013.01); G01N 2800/52 (2013.01)

(58) Field of Classification Search
None
See application file for complete search history.

(56) References Cited

U.S. PATENT DOCUMENTS

| | | |
|---|---|---|
| 5,691,151 A | 11/1997 | Braun et al. |
| 6,805,852 B2 | 10/2004 | Lin et al. |
| 6,861,053 B1 | 3/2005 | Lin et al. |
| 7,048,906 B2 | 5/2006 | Lin et al. |
| 7,056,686 B2 | 6/2006 | Lin et al. |
| 7,081,239 B2 | 7/2006 | Lin |
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |
| 7,608,245 B2 | 10/2009 | Lin |
| 7,615,207 B2 | 11/2009 | Lin |
| 7,718,608 B2 | 5/2010 | Lin et al. |
| 7,736,622 B2 | 6/2010 | Lin et al. |
| 7,935,799 B2 | 5/2011 | Lin et al. |
| 8,110,177 B2 | 2/2012 | Lin et al. |
| 8,197,805 B2 | 6/2012 | Lin et al. |
| 8,388,935 B2 | 3/2013 | Lin et al. |
| 8,562,952 B2 | 10/2013 | Lin |
| 9,110,081 B2 | 8/2015 | Pimentel et al. |
| 9,358,276 B2 | 6/2016 | Lin et al. |
| 9,851,361 B2 | 12/2017 | Pimentel |
| 9,869,676 B2 | 1/2018 | Pimentel et al. |
| 10,132,814 B2 | 11/2018 | Pimentel et al. |
| 10,151,752 B2 | 12/2018 | Pimentel et al. |
| 2003/0157159 A1 | 8/2003 | Franklin et al. |
| 2003/0170726 A1 | 9/2003 | Fradelizi et al. |
| 2004/0018528 A1 | 1/2004 | Morimoto et al. |
| 2004/0106590 A1 | 6/2004 | Eisenstein |
| 2006/0127359 A1 | 6/2006 | Borrelli |
| 2006/0193871 A1 | 8/2006 | Lin |
| 2007/0212691 A1 | 9/2007 | Yamasaki et al. |

(Continued)

FOREIGN PATENT DOCUMENTS

| | | |
|---|---|---|
| AU | 2002256254 B2 | 5/2007 |
| AU | 2007201246 A1 | 3/2009 |

(Continued)

OTHER PUBLICATIONS

PCT/US2010/023873 International Preliminary Report on Patentability dated Aug. 16, 2011.

(Continued)

*Primary Examiner* — Brian Gangle

(74) *Attorney, Agent, or Firm* — Linda B. Huber; Nixon Peabody LLP

(57) ABSTRACT

The present invention describes methods for preventing IBS, reducing the likelihood of developing IBS and/or treating IBS by administering CDT inhibitors and/or CDT neutralizers to a subject in need thereof. The present invention also describes methods of eliciting a specific immune response and methods of vaccinating a subject to prevent IBS or to reduce the likelihood of developing or having IBS. The present invention further describes methods of diagnosing IBS by detecting the presence or absence of CDT or a CDT marker in a subject.

23 Claims, 4 Drawing Sheets

Specification includes a Sequence Listing.

(56) References Cited

U.S. PATENT DOCUMENTS

| | | |
|---|---|---|
| 2009/0028940 A1 | 1/2009 | Jahagirdar et al. |
| 2009/0298060 A1 | 12/2009 | Lal et al. |
| 2011/0294726 A1 | 12/2011 | Pimentel et al. |
| 2013/0331283 A1 | 12/2013 | McAndrew et al. |
| 2014/0206636 A1 | 7/2014 | Lin et al. |
| 2017/0095543 A1 | 4/2017 | Lin et al. |
| 2018/0196063 A1 | 7/2018 | Pimentel et al. |
| 2019/0178890 A1 | 6/2019 | Pimentel et al. |
| 2019/0187153 A1 | 6/2019 | Pimentel et al. |

FOREIGN PATENT DOCUMENTS

| | | |
|---|---|---|
| AU | 2010213773 B2 | 10/2014 |
| AU | 2010213708 B2 | 12/2015 |
| AU | 2014331841 A1 | 3/2016 |
| AU | 2015330872 A1 | 4/2017 |
| AU | 2016201529 | 6/2018 |
| BR | 11 2016 00747-2 A2 | 9/2017 |
| CA | 2923651 A1 | 4/2015 |
| CA | 2962493 A1 | 4/2016 |
| CA | 2444548 C | 6/2016 |
| CA | 2922728 C | 2/2019 |
| CL | 2011-1944 | 2/2012 |
| CL | 2016000820 A1 | 9/2016 |
| CN | 105744956 A1 | 7/2016 |
| CN | 107003308 A | 8/2017 |
| CO | 16091069 | 9/2016 |
| EP | 1 385 476 | 2/2004 |
| EP | 1200828 | 10/2007 |
| EP | 2 256 498 A1 | 12/2010 |
| EP | 2 261 664 A2 | 12/2010 |
| EP | 2 261 665 A2 | 12/2010 |
| EP | 2 267 445 A1 | 12/2010 |
| EP | 2 305 213 A2 | 4/2011 |
| EP | 1811303 | 6/2011 |
| EP | 2 396 652 | 12/2011 |
| EP | 2267445 B1 | 8/2016 |
| EP | 3054977 A1 | 8/2016 |
| EP | 3204771 A1 | 8/2017 |
| EP | 2 396 652 B1 | 12/2017 |
| EP | 3349004 | 7/2018 |
| IN | 201727012044 A | 6/2017 |
| JP | 2009-102401 | 5/2009 |
| JP | 4653936 | 12/2010 |
| JP | 2017502253 A | 1/2017 |
| JP | 2017531801 A | 10/2017 |
| KR | 20160062161 A | 6/2016 |
| KR | 20170067795 A | 6/2017 |
| MX | 2016004167 A | 6/2016 |
| MX | 348670 | 6/2017 |
| MX | 2017055077 | 7/2017 |
| MX | 2017-045632 | 11/2017 |
| PE | 08822016 A1 | 9/2016 |
| RU | 2397178 C1 | 8/2010 |
| RU | 2683781 C2 | 4/2019 |
| SG | 11201601733V A | 4/2016 |
| SG | 11201702395W A | 4/2017 |
| SG | 11201601733V A | 5/2018 |
| WO | WO 92/06690 A1 | 4/1992 |
| WO | WO 01/11077 A2 | 2/2001 |
| WO | WO 2002/083926 A2 | 10/2002 |
| WO | 2005029091 A2 | 3/2005 |
| WO | WO 2006/102536 A2 | 9/2006 |
| WO | WO 2008/016708 A2 | 2/2008 |
| WO | WO 2009/108814 A1 | 9/2009 |
| WO | WO 2010/093776 A1 | 8/2010 |
| WO | WO 2010/093801 A1 | 8/2010 |
| WO | WO 2015/054529 B1 | 4/2015 |
| WO | WO 2016/057772 A1 | 4/2016 |
| WO | 2018140869 A1 | 8/2018 |

OTHER PUBLICATIONS

PCT/US2010/023873 International Search Report and Written Opinion dated Apr. 1, 2010, 7 Pages.
PCT/US2010/023911 International Preliminary Report on Patentability dated Aug. 16, 2011.
PCT/US2010/023911 International Search Report and Written Opinion dated May 14, 2010, 11 Pages.
PCT/US2014/059957 International Preliminary Report on Patentability dated Apr. 21, 2016; 9 pages.
PCT/US2014/059957 International Search Report and Written Opinion dated Jan. 8, 2015; 11 pages.
PCT/US2015/054655 International Search Report and Written Opinion dated Feb. 12, 2016; 7 pages.
International Search Report and Written Opinion of PCT/US2018/015723, dated Apr. 24, 2018, 13 Pages.
EP Application No. 14851688.3 Extended Search Report dated Mar. 10, 2017; 10 pages.
EP Application No. 10741728.9 Extended Search Report dated Oct. 17, 2014.
EP Application No. 10741713.1 Extended Search Report dated Jul. 27, 2012, 16 pages.
Extended European Search Report of EP 15849701.6 dated Feb. 8, 2018, 10 Pages.
EP Application No. 17206465.1 Extended Search Report dated Apr. 20, 2018; 13 pages.
Written Opinion of Singapore Application No. 11201601733V, dated Apr. 17, 2017; 8 pages.
SG 11201702395W Written Opinion dated Nov. 24, 2017, 8 pages.
Abuoun et al. Cytolethal Distending Toxin (CDT)-Negative Campylobacter jejuni Strains and Anti-CDT Neutralizing Antibodies are Induced during Human Infection but Not during Colonization in Chickens. Infection and Immunity (2005). 73(5): 3053-3062.
Air et al. Mechanism of Antigenic Variation in an Individual Epitope on Influenza Virus N9 Neuraminidase. Journal of Virology (1990). 64(12):5797-5803.
American College of Gastroenterology Task Force on IBS. An Evidence-Based Position Statement on the Management of Irritable Bowel Syndrome. The American Journal of Gastroenterology (2009). 104(S1): S1-35.
Bourke, B. Campylobacter infection: small bowel and colon. Current Opinion in Gastroenterology. (2002). 18:4-9.
Bradesi et al., Novel Therapeutic Approaches in IBS, Current Opinion in Pharmacology, 2007, vol. 7(6), pp. 598-604.
Colman, PM. Effects of amino acid sequence changes on antibody-antigen interactions. Res Immunol (1994). 145(1):33-6.
Connor, B.A. Sequelae of Traveler's Diarrhea: Focus on Postinfectious Irritable Bowel Syndrome. Clinical Infectious Diseases (2005). 41(S8):S577-586.
Dib et al., Targets of Anti-Endothelial Cell Antibodies in Pulmonary Hypertension and Scleroderma, 2012, Eur. Respir. J., vol. 39, pp. 1405-1414.
Dunlop et al. Relative Importance of Enterochromaffin Cell Hyperplasia, Anxiety, and Depression in Postinfectious IBS. Gastroenterology (2003). 125:1651-1659.
Dupont, A. et al. Travelers' Diarrhea: Modern Concepts and New Developments. Current Treatment Option in Gastroenterology. Database Medline: US National Library of Medicine. (2006). Abstract Only.
Dupont, H. Postinfectious Irritable Bowel Syndrome: Clinical Aspects, Pathophysiology, and Treatment. Practical Gastroenterology (2007). 31(S9): 18-24.
Fox et al. Gastroenteritis in NF-kappaB-deficient mice is produced with wildtype Campylobacter jejuni but not with C. jejuni lacking cytolethal distending toxin despite persistent colonization with both strains. Infection & Immunity (2004). 72(2):1116-25.
Halsey, J. Current and Future Treatment Modalities for Clostridium-difficile-Associated Disease. Am J. Health-Syst Pharm (2008). 65:705-715.
Hickey et al. Campylobacter jejuni Cytolethal Distending Toxin Mediates Release of Interleukin-8 from Intestinal Epithelial Cells. Infection and Immunity (2000). 68(12):6535-6541.

(56) References Cited

OTHER PUBLICATIONS

Jee et al. Antibiotics and Cdt Expression in Campylobacter Jejuni Contribute to Duration of Colonization in Rats. Gastroenterology. (2008). 134(4). Abstract Only.
Johnson et al. Interruption of Recurrent Clostridium difficile-Associated Diarrhea Episodes by Serial Therapy with Vancomycin and Rifaximin. Clinical Infectious Diseases (2007). 44:846-848.
Kokkotou et al. Comparative Efficacies of Rifaximin and Vancomycin for Treatment of Clostridium difficile-Associated Diarrhea and Prevention of Disease Recurrence in Hamsters. Antimicrobial Agents and Chemotherapy (2008). 52(3): 1121-1126.
Lembo et al. Use of serum biomarkers in a diagnostic test for irritable bowel syndrome. Alimentary Pharmacology & Therapeutics (2009). 29:834-842.
Mariuzza et al. The structural basis of antigen-antibody recognition. Annu Rev Biophys Biophys Chem (1987). 16:139-59. Abstract Only.
Medindia. IBS Sufferers Benefited by Non-Absorbable Antibiotics. (2006). Retrieved from Internet: www.medindia.net/news/view_newsmain.asp?x=15225.
Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.
Morales et al. Effect of Rifaximin Treatment on Anti-Vinculin Antibodies in IBS with Diarrhea. Gastroenterology (2016).150(4). Supplement 1. p. S-695.
Morales et al. Tu2056 Antibodies to Cytolethal Distending Toxin B and Auto-Antibodies to Human Vinculin are Elevated in IBS Subjects. Gastroenterology (2013). 144(5): Suppl 1, p. S-914.
Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.
Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.
Novak et al. A Serologic Test for Irritable Bowel Syndrome and Other News from ACG. Gastroenterology Press Highlights (2013). 2 pages.
Pimentel et al. A New Rat Model Links Two Complementary Theories in Irritable Bowel Syndrome. Digestive Diseases and Sciences (2007). 53(4):982-989.
Pimentel et al. Anti-vinculin antibodies: Multicenter validation of a diagnostic blood test for irritable bowel syndrome. The American Journal of Gastroenterology (2013). 108:1887; p. S571. Abstract Only.
Pimentel et al. Autoimmunity to vinculin in humans may be important in the pathophysiology of IBS. Gastroenterology (2014). 146(5); suppl 1, Su2020. Abstract Only.
Pimentel et al. Development and Validation of a Biomarker for Diarrhea-Predominant Irritable Bowel Syndrome in Human Subjects. PloS One (2015). 10(5):e0126438: 12 pages.
Purdy et a. Characterisation of cytolethal distending toxin (CDT) mutants of Campylobacter jejuni. J. Med. Microbiol. (2000). 49: pp. 473-479.
Regent et al., Identification of Target Antigens of Anti-Endothelial Cell and Anti-Vascular Smooth Muscle Cell Antigodies in Patients with Giant Cell Arteritis: a Proteomic Approach, 2011, Arthritis Research & Therapy, 13: R107, 15 Pages.
Rezaie et al. Assessment of Anti-Vinculin and Anti-CdtB Antibodies in IBS Subtypes. Gastroenterology (2016).150(4). Supplement 1. p. S62.
Rezaie et al. Assessment of Anti-Vinculin and Anti-Cytolethal Distending Toxin B Antibodies in Subtypes of Irritable Bowel Syndrome, 20167, Digestive Diseases and Sciences, vol. 62(6), pp. 1480-1485.
Sabota et al. A New Variant of Food Poisoning: Enteroinvasive Klebsiella Pneumoniae and *Escherichia coli* Sepsis from a Contaminated Hamburger. The American Journal of Gastroenterology (1998). 93(1): 118-119.
Science Daily. Irritable Bowel Syndrome Study Shows that Targeted Antibiotics Lead to Long-Lasting Improvement in Symptoms. (2005). Retrieved from Internet: http://www.sciencedaily.com/releases/2005/11/051109181127.htm.
Spiller et al. Increased rectal mucosal enteroendocrine cells,T lymphocytes, and increased gut permeability following acute Campylobacter enteritis and in post-dysenteric irritable bowel syndrome. Gut (2000). 47:804-811.
Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.
Taylor et al. Rifaximin, a Nonabsorbed Oral Antibiotic, Prevents Shigellosis after Experimental Challenge. Clinical Infectious Diseases. (2006). 42:1283-1288.
Trees et al. Genome Sequences of 228 Shiga Toxin-Producing *Escherichia coli* Isolates and 12 Isolates Representing Other Diarrheagenic *E. coli* Pathotypes. Genome Announc (2014). 2(4): 3 pages.
Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Su1424. Abstract Only.
Turkay et al. Noninvasive methods in evaluation of inflammatory bowel disease: where do we stand now? An update. Clinics (2010). 65(2):221-31.
Office Action of RU 2016116766, dated Jul. 25, 2018, 12 Pages.
Jee et al., ICC Density Predicts Bacterial Overgrowth in a Rat Model of Post-Infectious IBS, 2010, World J. Gastroenterol, vol. 16(29), pp. 3680-3686.
Mark Pimentel, Evaluating a bacterial hypothesis in IBS using a modification of Koch's postulates: part 1, 2010, Am J Gastroenterol, vol. 105, pp. 718-721.
Weller et al., Complete Sequence of Human Vinculin and Assignment of the Gene to Chromosome 10, 1990, Proceedings of the National Academy of Sciences of the USA, vol. 87, pp. 5667-5671.
Pandey et al., Association of Cytolethal Distending Toxin Locus cdtB with Enteropathogenic *Escherichia coli* Isolated from Patients with Acute Diarrhea in Calcutta, India, 2003, J. Clin. Microbiol., vol. 41(11), pp. 5277-5281.

FIG. 1

MKKIVFLILSFNVLFAALENYNTGTWNLQGSSAATESKWNVSIRQLITGANPMD
VLAVQEAGVLPSTAMMTPRQVQPVGVGIPIHEYIWNLGSVSRPSSVYIYYSRV
DVGANRVNLAIVSRVQADEVFVLPPPTVASRPIIGIRIGNDAFFNIHALASGGND
AGAIVAAVDMFFRNRPDINWMILGDFNRESGALVTLLDPDLRARTRVVVPPSS
TQTSGRTIDYAITGNSNTAALYNPPPIVAILALEGLRTFLASDHFPVNFRRP (SEQ ID NO:1)

FIG. 2 atgaaaaaaa tagtattttt gattttaagt tttaatgtat tatttgccgc tttagaaaat    60
tacaacaccg gaacttggaa tttgcaaggc tcatcagctg caactgaaag caaatggaat    120
gttagtataa gacaactcat aaccggtgca aatcctatgg atgttttagc tgttcaagaa    180
gcgggggttt tacctagtac agctatgatg actcctagac aggtacaacc cgtgggcgtg    240
ggtattccta tacatgaata catatggaat ttaggctctg tatcaagacc tagctctgtt    300
tatatatatt attctagagt ggatgtagga gcaaatcgtg tgaatttagc tatcgttagc    360
agagtgcaag cggatgaagt ttttgttta cccctccaa cagttgcttc aagacctatt    420
ataggcatac gcataggcaa tgatgctttt tcaatatac acgctctagc aagtggggga    480
aatgacgcag gagccattgt cgctgctgtg gatatgtttt ttagaaatag acctgatatt    540
aattggatga ttttaggcga ttttaataga gaatcaggcg ccttagtaac cttgctagat    600
cctgacttaa gagcacgcac tcgcgtagtt gttccgcctt cttctacgca aacaagtgga    660
agaacgattg attatgctat cactggaaat tccaacactg cagctttata caacccacca    720
ccgatagttg cgattttagc tttagaagga ttaagaacct ttttggcttc agatcatttt    780
cctgtaaatt ttagaagacc ttag    804

(SEQ ID NO:2)

FIG. 4

MKKIICLFLSFNLAFANLENFNVGTWNLQGSSAATESKWSVSVRQLVSGANPLDILMIQE
AGTLPRTATPTGRHVQQGGTPIDEYEWNLGTLSRPDRVFIYYSRVDVGANRVNLAIVSRM
QAEEVIVLPPPTTVSRPIIGIRNGNDAFFNIHALANGGTDVGAIITAVDAHFANMPQVNW
MIAGDFNRDPSTITSTVDRELANRIRVVFPTSATQASGGTLDYAITGNSRQQTYTPPLL
AAILMLASLRSHIVSDHFPVNFRKF (SEQ ID NO:5)

SEQUENCE LISTING

<160> NUMBER OF SEQ ID NOS: 6

<210> SEQ ID NO 1
<211> LENGTH: 267
<212> TYPE: PRT
<213> ORGANISM: Campylobacter coli

<400> SEQUENCE: 1

Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu
    50                  55                  60

Pro Ser Thr Ala Met Met Thr Pro Arg Gln Val Gln Pro Val Gly Val
65                  70                  75                  80

Gly Ile Pro Ile His Glu Tyr Ile Trp Asn Leu Gly Ser Val Ser Arg
                85                  90                  95

Pro Ser Ser Val Tyr Ile Tyr Tyr Ser Arg Val Asp Val Gly Ala Asn
            100                 105                 110

Arg Val Asn Leu Ala Ile Val Ser Arg Val Gln Ala Asp Glu Val Phe
        115                 120                 125

Val Leu Pro Pro Pro Thr Val Ala Ser Arg Pro Ile Ile Gly Ile Arg
    130                 135                 140

Ile Gly Asn Asp Ala Phe Phe Asn Ile His Ala Leu Ala Ser Gly Gly
145                 150                 155                 160

Asn Asp Ala Gly Ala Ile Val Ala Ala Val Asp Met Phe Phe Arg Asn
                165                 170                 175

Arg Pro Asp Ile Asn Trp Met Ile Leu Gly Asp Phe Asn Arg Glu Ser
            180                 185                 190

Gly Ala Leu Val Thr Leu Leu Asp Pro Asp Leu Arg Ala Arg Thr Arg
        195                 200                 205

Val Val Val Pro Pro Ser Ser Thr Gln Thr Ser Gly Arg Thr Ile Asp
    210                 215                 220

Tyr Ala Ile Thr Gly Asn Ser Asn Thr Ala Ala Leu Tyr Asn Pro Pro
225                 230                 235                 240

Pro Ile Val Ala Ile Leu Ala Leu Glu Gly Leu Arg Thr Phe Leu Ala
                245                 250                 255

Ser Asp His Phe Pro Val Asn Phe Arg Arg Pro
            260                 265

<210> SEQ ID NO 2
<211> LENGTH: 804
<212> TYPE: DNA
<213> ORGANISM: Campylobacter coli

<400> SEQUENCE: 2
atgaaaaaaa tagtattttt gattttaagt tttaatgtat tatttgccgc tttagaaaat     60
tacaacaccg gaacttggaa tttgcaaggc tcatcagctg caactgaaag caaatggaat    120
gttagtataa gacaactcat aaccggtgca atcctatgg atgttttagc tgttcaagaa    180
gcgggggttt tacctagtac agctatgatg actcctagac aggtacaacc cgtgggcgtg    240
ggtattccta tacatgaata catatggaat ttaggctctg tatcaagacc tagctctgtt    300

```
tatatatatt attctagagt ggatgtagga gcaaatcgtg tgaatttagc tatcgttagc    360
agagtgcaag cggatgaagt ttttgtttta ccccctccaa cagttgcttc aagacctat    420 ataggcatac gcataggcaa tgatgctttt ttcaatatac acgctctagc aagtggggga    480
aatgacgcag gagccattgt cgctgctgtg gatatgtttt ttagaaatag acctgatatt    540
aattggatga ttttaggcga ttttaataga gaatcaggcg ccttagtaac cttgctagat    600
cctgacttaa gagcacgcac tcgcgtagtt gttccgcctt cttctacgca aacaagtgga    660
agaacgattg attatgctat cactggaaat tccaacactg cagctttata acccaccca    720 ccgatagttg cgattttagc tttagaagga ttaagaacct ttttggcttc agatcatttt    780
cctgtaaatt ttagaagacc ttag                                          804
```

<210> SEQ ID NO 3  
<211> LENGTH: 17  
<212> TYPE: PRT  
<213> ORGANISM: Campylobacter jejuni

<400> SEQUENCE: 3

```
Leu Asp Tyr Ala Ile Thr Gly Asn Ser Asn Arg Gln Gln Thr Tyr Thr
1               5                   10                  15

Pro
```

<210> SEQ ID NO 4  
<211> LENGTH: 18  
<212> TYPE: PRT  
<213> ORGANISM: Artificial Sequence  
<220> FEATURE:  
<223> OTHER INFORMATION: synthetic construct

<400> SEQUENCE: 4

```
Cys Leu Asp Tyr Ala Ile Thr Gly Asn Ser Asn Arg Gln Gln Thr Tyr
1               5                   10                  15

Thr Pro
```

<210> SEQ ID NO 5  
<211> LENGTH: 265  
<212> TYPE: PRT  
<213> ORGANISM: Campylobacter jejuni

<400> SEQUENCE: 5

```
Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
                20                  25                  30

Ala Ala Thr Glu Ser Lys Trp Ser Val Ser Val Arg Gln Leu Val Ser
            35                  40                  45

Gly Ala Asn Pro Leu Asp Ile Leu Met Ile Gln Glu Ala Gly Thr Leu
        50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
                100                 105                 110

Asn Leu Ala Ile Val Ser Arg Met Gln Ala Glu Glu Val Ile Val Leu
            115                 120                 125

Pro Pro Pro Thr Thr Val Ser Arg Pro Ile Ile Gly Ile Arg Asn Gly
```

```
                   130                 135                 140
Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
                180                 185                 190

Ile Thr Ser Thr Val Asp Arg Glu Leu Ala Asn Arg Ile Arg Val Val
                195                 200                 205

Phe Pro Thr Ser Ala Thr Gln Ala Ser Gly Gly Thr Leu Asp Tyr Ala
            210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
                260                 265

<210> SEQ ID NO 6
<211> LENGTH: 51
<212> TYPE: DNA
<213> ORGANISM: Campylobacter jejuni

<400> SEQUENCE: 6
cttgattatg caattacagg aaattcaaat agacaacaaa cctatactcc a          51
```

ANTIBODY TO CYTOLETHAL DISTENDING TOXIN OF CAMPYLOBACTER JEJUNI

CROSS-REFERENCE TO RELATED APPLICATIONS

This application is a continuation of Ser. No. 15/855,792, filed Dec. 27, 2017, which is a continuation of U.S. patent application Ser. No. 14/793,523 filed Jul. 7, 2015, now U.S. Pat. No. 9,869,676, which is a continuation of U.S. patent application Ser. No. 13/148,252 filed Aug. 5, 2011, now U.S. Pat. No. 9,110,081, which is the National Phase of International Application No. PCT/2010/023911, filed Feb. 11, 2010, which designated the U.S. and that International Application was published under PCT Article 21(2) in English, which claims the benefit of and priority under 35 U.S.C. § 119(e) to U.S. provisional patent application No. 61/151,779 filed Feb. 11, 2009, and U.S. provisional patent application No. 61/286,250 filed Dec. 14, 2009, the entirety of which is hereby incorporated by reference.

FIELD OF INVENTION

This invention relates to the diagnosis, treatment and prevention of irritable bowel syndrome.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cytolethal distending toxin (CDT) is a bacterial protein toxin produced by several pathogenic bacteria. CDT is composed of three subunits, CdtA, CdtB and CdtC, which together form a ternary complex. CdtB is the active component, and CdtA and CdtC are involved in delivering CdtB into the cells. CDT controls host cells by CdtB-mediated limited DNA damage of the host cell chromosome, which triggers the response of the cell cycle checkpoint and results in G2 arrest in the cells. CDT also induces apoptotic cell death of lymphocytes, which may be relevant to onset or persistence of chronic infection by the producing bacteria. (Ohara et al., J. Biochem, 2004, Vol. 136, No. 4 409-413.) Additionally, the presence of CdtB is universal among bacteria that cause food poisoning (e.g., *Campylobacter* (e.g., *C. jejuni, C. coli*), *Escherichia coli* (e.g., enterotoxigenic *E. coli* (ETEC), enterohaemorrhagic *E. coli* (EHEC), enteropathogenic *E. coli* (EPEC)), *Salmonella, Shigella,* and *Clostridium difficile*).

Irritable bowel syndrome ("IBS") is a disorder characterized by, inter alia, cramping, abdominal pain, bloating, constipation, and diarrhea. IBS can cause a great deal of discomfort and distress. While many people can control their symptoms with diet, stress management, and medications, for some people IBS can be disabling. They may be unable to work, attend social events, or even travel short distances. As many as 20% of the adult population have symptoms of IBS; making it one of the most common disorders diagnosed by doctors.

In addition to irritable bowel syndrome, another phenomenon linked to IBS is non-ulcer dyspepsia (NUD). This is a condition whereby subjects experience discomfort in the upper abdominal area that cannot be explained by findings on an endoscopy such as an ulcer or irritation of the lining of stomach or intestine. This condition is another of the functional bowel conditions. There is a general recognition that very often there is an overlap between IBS and NUD to a degree that is more than just common occurrence (Talley et al., *The association between non-ulcer dyspepsia and other gastrointestinal disorders.* SCANS J GASTROENTEROL 1985; 20:896-900). In addition, recent evidence suggests that acute gastroenteritis can precipitate IBS and NUD (Mearin et al., *Dyspepsia and irritable bowel syndrome after a Salmonella and gastroenteritis outbreak: One year follow up cohort study.* GASTROENTEROL 2005; 129:98-104.). This evidence suggests that the pathophysiology of IBS and NUD may be linked to this initial food poisoning insult. As such, it is likely that the same mechanisms are in play.

Accordingly, there exists a need for diagnosis, treatment, prevention and reduction of the likelihood of having or developing IBS as well as NUD. Heretofore, there has been no association between CDT and IBS or CDT and NUD. Based upon the inventors' findings, therapies and diagnostics based on the association between CDT and IBS as described herein can be beneficial for IBS subjects, to prevent or reduce a subject's likelihood of developing IBS and/or NUD.

SUMMARY OF THE INVENTION

The following embodiments and aspects thereof are described and illustrated in conjunction with compositions and methods which are meant to be exemplary and illustrative, not limiting in scope.

The present invention provides for a method, comprising: obtaining a biological sample from a subject selected from the group consisting of: a subject in need of a diagnosis regarding irritable bowel syndrome (IBS), a subject in need of a diagnosis regarding a subset of IBS, a subject in need of a determination of a likelihood of having or developing IBS, a subject in need of a determination of a likelihood of having or developing a subset of IBS, a subject in need of a diagnosis regarding non-ulcer dyspepsia (NUD), a subject in need of a determination regarding small intestinal bacterial overgrowth (SIBO), a subject in need of a determination of a susceptibility to having SIBO, a subject who desires a prognosis of a response to antibiotic treatment for IBS, a subject who desires a prognosis of a response to antibiotic treatment to reduce the likelihood of having IBS and combinations thereof; detecting the presence or absence of cytolethal distending toxin (CDT) or one or more markers of CDT in the biological sample; and correlating the presence of CDT or one or more markers of CDT with a likely presence of IBS, a likely presence of a subset of IBS, a likelihood of having or developing IBS, a likelihood of having or developing a subset of IBS a likely presence of NUD, a likely presence of SIBO, a higher susceptibility to having SIBO, a higher likelihood of having a beneficial result from antibiotic treatment for IBS, and/or a higher likelihood of having a beneficial result from antibiotic treatment to reduce the likelihood of having IBS, or correlating an absence of CDT and an absence of one or more markers of CDT with a likely absence of IBS, a likely absence of the subset of IBS, a lower likelihood of having or developing IBS, a lower likelihood of having or developing the subset of IBS, a likely absence of NUD, a likely absence of SIBO, a lower susceptibility to having SIBO, a lower likelihood of having a beneficial result from antibiotic treatment for IBS, and/or a lower likelihood of having a beneficial result from antibiotic treatment to reduce the likelihood of having IBS.

In one embodiment, the method may further comprise identifying the subject in need of the diagnosis regarding IBS, the subject in need of the diagnosis regarding the subset of IBS, the subject in need of the determination of the likelihood of having or developing IBS, the subject in need of the determination of the likelihood of having or developing subset of IBS, the subject in need of the diagnosis regarding NUD, the subject in need of the determination regarding SIBO, the subject in need of the determination of the susceptibility to having SIBO, the subject who desires the prognosis of the response to antibiotic treatment for IBS, and/or the subject who desires the prognosis of the response to antibiotic treatment to reduce the likelihood of having IBS.

In another embodiment, the method may further comprise choosing an antibiotic therapy for the subject based on the likely presence of IBS, the likely presence of the subset of IBS, the likelihood of having or developing IBS, the likelihood of having or developing the subset of IBS, the likely presence of NUD, the likely presence of SIBO, the higher susceptibility to having SIBO, the higher likelihood of having the beneficial result from antibiotic treatment for IBS, and/or the higher likelihood of having the beneficial result from antibiotic treatment to reduce the likelihood of having IBS.

In one embodiment, the subset of IBS may be selected from the group consisting of constipation-predominant IBS, diarrhea-predominant IBS, mixed IBS, undetermined IBS, and antibiotic responsive IBS.

In a certain embodiment, the one or more markers of CDT may be an antibody capable of binding specifically to CDT, CdtA, CdtB, CdtC or a fragment thereof. In one embodiment, the CdtB may be CdtB of *Campylobacter jejuni*. In a certain embodiment, the CdtB of *Campylobacter jejuni* has an amino acid sequence at least 80% identical to SEQ ID NO:5.

In another embodiment, the antibody is capable of binding specifically to an epitope on 5 to 22 contiguous residues of SEQ ID NO:5. In a certain embodiment, the epitope may be on 17 contiguous residues as disclosed by SEQ ID NO:3. In another embodiment, the antibody may be capable of binding specifically to an epitope on SEQ ID NO:4.

In another embodiment, the CdtB may be CdtB of *Campylobacter coli* and has an amino acid sequence at least 80% identical to SEQ ID NO:1. In another embodiment, the CdtB may be CdtB of *Escherichia coli, Salmonella, Shigella*, or *Clostridium difficile*.

The present invention also provides for a method, comprising: providing a composition to elicit a specific immune response, comprising: an agent selected from the group consisting of a fragment of cytolethal distending toxin (CDT) incapable of causing irritable bowel syndrome (IBS), CdtA incapable of causing IBS, CdtB incapable of causing IBS, CdtC incapable of causing IBS, CDT mutein incapable of causing IBS, a fragment of CDT mutein incapable of causing IBS, CdtA mutein incapable of causing IBS, CdtB mutein incapable of causing IBS, CdtC mutein incapable of causing IBS, a bacterium comprising a mutated CDT gene rendering the bacterium incapable of causing IBS, and combinations thereof; and administering the composition to a subject in need thereof to elicit a specific immune response. In various embodiments, eliciting the specific immune response reduces the subject's likelihood of developing or having IBS, or reduces the subject's likelihood of developing or having non-ulcer dyspepsia (NUD).

In one embodiment, the bacterium may be *Campylobacter jejuni* 81-176 that failed to express a functional cytolethal distending toxin B (CdtB) due to an insertion mutation at the gene for CdtB. In a certain embodiment, the bacterium may be killed. In another embodiment, the bacterium may be attenuated.

The present invention also provides for a method, comprising: providing a cytolethal distending toxin (CDT) inhibitor and/or a CDT neutralizer to reduce the likelihood of developing or having irritable bowel syndrome (IBS) or to reduce the likelihood of developing or having non-ulcer dyspepsia (NUD); and administering the CDT inhibitor and/or the CDT neutralizer to a subject in need thereof.

In one embodiment, the CDT inhibitor and/or the CDT neutralizer may be an antibody capable of binding specifically to CDT or a subunit of CDT. In one embodiment, the subunit of CDT may be CdtB. In a certain embodiment, the CdtB may be CdtB of *Campylobacter jejuni*. In a certain embodiment, the CdtB of *Campylobacter jejuni* may have an amino acid sequence at least 80% identical to SEQ ID NO:5.

In another embodiment, the antibody binds specifically to an epitope on 5 to 22 contiguous residues of SEQ ID NO:5. In another embodiment, the epitope is on 17 contiguous residues as disclosed by SEQ ID NO:3.

In another embodiment, the antibody is capable of binding specifically to an epitope on SEQ ID NO:4.

In another embodiment, the CdtB may be CdtB of *Campylobacter coli* and may have an amino acid sequence at least 80% identical to SEQ ID NO:1. In another embodiment, the CdtB may be CdtB of *Escherichia coli, Salmonella, Shigella* or *Clostridium difficile*.

The present invention also provides a purified antibody that binds specifically to cytolethal distending toxin (CDT) a subunit of CDT and inhibits or neutralizes CDT or the subunit of CDT. In one embodiment, the subunit of CDT may be CdtB. In a certain embodiment, the CdtB may be CdtB of *Campylobacter jejuni*. In one embodiment, the CdtB of *Campylobacter jejuni* may have an amino acid sequence at least 80% identical to SEQ ID NO:5.

In another embodiment, the purified antibody binds specifically to an epitope on 5 to 22 contiguous residues of SEQ ID NO:5 In one embodiment, the epitope may be on 17 contiguous residues as disclosed by SEQ ID NO:3.

In another embodiment, the purified antibody binds specifically to an epitope on SEQ ID NO:4.

In another embodiment, the CdtB is CdtB of *Campylobacter coli* and has an amino acid sequence at least 80% identical to SEQ ID NO:1.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts the amino acid sequence of CdtB of *Campylobacter coli* (SEQ ID NO:1) in accordance with an embodiment of the present invention.

FIG. 2 depicts the nucleic acid sequence of CdtB of *Campylobacter coli* (SEQ ID NO:2) in accordance with an embodiment of the present invention.

FIG. 4 depicts the amino acid sequence of CdtB of *Campylobacter jejuni* subsp. *jejuni* 81-176 (SEQ ID NO:5) in accordance with an embodiment of the present invention.

DESCRIPTION OF THE INVENTION

Figure 3:
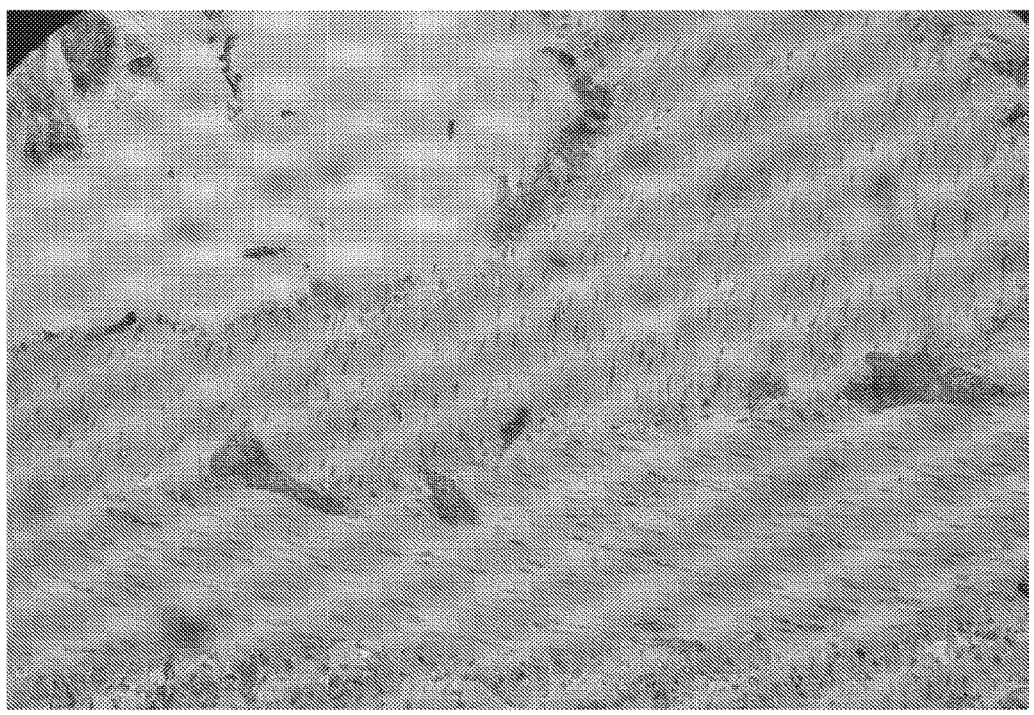
FIG. 3 depicts a nerve stained with antibodies against CdtB in accordance with an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. For references on how to prepare antibodies described herein, see D. Lane, *Antibodies: A Laboratory Manual* (Cold Spring Harbor Press, Cold Spring Harbor N.Y., 1988); Kohler and Milstein, (1976) Eur. J. Immunol. 6: 511; Queen et al. U.S. Pat. No. 5,585,089; and Riechmann et al., Nature 332: 323 (1988).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, slowing down the progression of the disease condition, preventing the development of the disease condition, reducing the likelihood of developing the disease condition, and curing the disease condition.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult and newborn subjects, as well as fetuses, whether male or female, are intended to be including within the scope of this term.

"Conditions" and "disease conditions," as used herein may include, but are in no way limited to any form of irritable bowel syndrome (e.g., diarrhea-predominant, constipation-predominant, mixed (constipation and diarrhea), and undetermined), altered bowel function, and irregular bowel pattern.

"Irregular bowel pattern" as used herein refers to a change in the consistency of stool form and/or a change in the frequency of bowel movements.

"Treatment" and "treating," as used herein refer to both therapeutic treatment and prophylactic or preventative measures (e.g., to reduce the likelihood of having the condition or disease condition), wherein the object is to prevent or slow down (lessen) the targeted pathologic condition or disorder even if the treatment is ultimately unsuccessful. Those in need of treatment include those already with the condition or disorder as well as those prone to have the condition or disorder or those in whom the condition or disorder is to be prevented (e.g., reducing the likelihood of having the condition or disorder).

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

"Purified" antibody as used herein refers to an antibody which has been identified, separated and/or recovered from a component of its natural environment. For example, composition comprising an antibody as described herein will be purified from a cell culture or other synthetic environment to greater than 60%, 70%, 80%, 85%, 90%, 95%, 96%, 97%, 98%, or 99% by weight of the antibody.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"CDT mutein" and "mutein of CDT" refer to a CDT molecule or a CDT subunit having one or more amino acids that have been mutated to alter its properties (e.g., inability to cause conditions or disease conditions described herein, capability to elicit a specific immune response and/or to serve as a vaccine). Mutations include substitution, deletion and/or insertion of one or more amino acids.

In a new post-infectious rat model designed to investigate the pathophysiology of irritable bowel syndrome (IBS), rats developed altered stool form 3 months after clearance of *Campylobacter jejuni* infection. A common toxin among the numerous bacterial pathogens known to cause acute gastroenteritis and post-infectious IBS is cytolethal distending toxin (CDT). The inventors aimed to determine if CDT plays a role in the long term altered bowel function after gastroenteritis using a rat model of post-infectious IBS. The inventors found that CDT is important in the development of chronic altered bowel function in a rat model of post-infectious IBS. Rats exposed to a *Campylobacter* strain that was deficient in CDT had bowel patterns more consistent with normal rats.

Further, the inventors discovered that two distinct antibodies to the B subunit of the cytolethal distending toxin both appear to bind rat intestinal neuromuscular elements even in the absence of previous exposure to *C. jejuni*. This finding suggests that anti-CdtB antibodies may be reacting to a host protein or structure with sequence homology or structural similarity to CdtB. It also raises the possibility that molecular mimicry and aberrant host immune responses may mediate chronic GI sequelae (e.g., PI-IBS) of *C. jejuni* infection. As such, there may be a protein on nerves that is similar to CDT and the immune system is reacting to that protein after infection with *C. jejuni*. This can cause long term disturbance in bowel function. Thus, detecting the antibody in human bloodstream could allow for the diagnosis of IBS.

Various embodiments of the present invention are based on the findings that CDT is important in the development of chronic altered bowel function in a rat model of postinfectious IBS and that anti-CdtB antibodies may be reacting to a host protein with homology to CdtB.

Various embodiments of the present invention provide agents capable of inhibiting and/or neutralizing CDT ("CDT inhibitor" and "CDT neutralizer").

In various embodiments, the agent is a purified antibody that binds specifically to CDT and inhibits and/or neutralizes the activity of CDT. These antibodies are also useful for additional purposes, such as diagnosing a subject's likelihood of having IBS, as discussed below. The amino acid sequences of CDT are known in the art.

In one embodiment, the purified antibody specifically binds to an epitope on the receptor-binding domain of CDT.

In another embodiment, the purified antibody binds specifically to the CdtA subunit of CDT. In another embodiment, the purified antibody binds specifically to the CdtB subunit of CDT. In another embodiment, the purified antibody binds specifically to the CdtC subunit of CDT.

An example of a CdtB amino acid sequence is *Campylobacter jejuni* cytolethal distending toxin B, which has the amino acid sequence (SEQ ID NO: 5) as shown in FIG. 4.

Another example of a CdtB amino acid sequence is *Campylobacter coli* cytolethal distending toxin B, which has the amino acid sequence (SEQ ID NO: 1) and nucleic acid sequence (SEQ ID NO:2), as shown in FIGS. 1 and 2, respectively.

Accordingly, in one embodiment, the purified antibody binds specifically to SEQ ID NO:5 (CdtB of *C. jejuni*). In various embodiments, the purified antibody binds specifically to an amino acid sequence at least 80%, 85%, 90%, 95%, 96%, 97%, 98%, or 99% identical to SEQ ID NO: 5.

In another embodiment, the purified antibody binds specifically to SEQ ID NO:1 (CdtB of *C. coli*). In various embodiments, the purified antibody binds specifically to an amino acid sequence at least 80%, 85%, 90%, 95%, 96%, 97%, 98%, or 99% identical to SEQ ID NO: 1.

In another embodiment, the purified antibody binds specifically to a 17 residue peptide of CdtB (e.g., 17 residues of SEQ. ID NOs: 1 or 5). In one embodiment, the 17 residue peptide has the following sequence: LDYAITGNSNRQQTYTP (SEQ ID NO:3).

In other embodiments, the antibody binds specifically to a 17 residue peptide that has at least 80%, 85%, 90%, 95%, 96%, 97%, 98%, 99% or 100% homology with 17 contiguous residues of CdtB (e.g., 17 contiguous residues of SEQ. ID NOs: 1 or 5). In one embodiment, the 17 residues of CdtB have the following sequence: LDYAITGNSNRQQTYTP (SEQ ID NO:3).

In other embodiments, the antibody binds specifically to a polypeptide comprising 17 residues that have at least 80%, 85%, 90%, 95%, 96%, 97%, 98%, 99% or 100% homology with 17 contiguous residues of CdtB (e.g., 17 residues of SEQ. ID NOs: 1 or 5). In one embodiment, the 17 contiguous residues of CdtB have the following sequence: LDYAITGNSNRQQTYTP (SEQ ID NO:3).

In another embodiment, the purified antibody binds specifically to an 18 residue peptide having the following sequence: CLDYAITGNSNRQQTYTP (SEQ ID NO:4). The cysteine at the N-terminus was added to SEQ ID NO:3 for purposes of conjugation.

In other embodiments, the antibody binds specifically to a polypeptide comprising 18 residues that have at least 80%, 85%, 90%, 95%, 96%, 97%, 98%, 99% or 100% homology to CLDYAITGNSNRQQTYTP (SEQ ID NO:4).

In another embodiment, the purified antibody binds specifically to a 5, 6, 7, 8, 9, 10, 11, 12, 13, 14, 15, 16, 17, 18, 19, 20, 21, or 22 residue peptide that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). In another embodiment, the purified antibody binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). Contiguous residues of SEQ ID NO:1 include those beginning at any amino acid and ending at any amino acid of SEQ ID NO:1. Contiguous residues of SEQ ID NO:5 include those beginning at any amino acid and ending at any amino acid of SEQ ID NO:5.

In another embodiment, the purified antibody binds specifically to a 5, 6, 7, 8, 9, 10, 11, 12, 13, 14, 15, 16, or 17 residue peptide that has at least 80%, 85%, 90%, 95%, 96%, 97%, 98%, 99% or 100% homology with 5, 6, 7, 8, 9, 10, 11, 12, 13, 14, 15, 16, or 17 contiguous residues of LDYAITGNSNRQQTYTP (SEQ ID NO:3) (e.g., 5, 6, 7, 8, 9, 10, 11, 12, 13, 14, 15, 16, or 17 contiguous residues of SEQ ID NO:3). In another embodiment, the purified antibody binds specifically to a polypeptide comprising 5, 6, 7, 8, 9, 10, 11, 12, 13, 14, 15, 16, or 17 residues that has at least 80%, 85%, 90%, 95%, 96%, 97%, 98%, 99% or 100% homology with 5, 6, 7, 8, 9, 10, 11, 12, 13, 14, 15, 16, or 17 contiguous residues of SEQ ID NO:3 (e.g., 5, 6, 7, 8, 9, 10, 11, 12, 13, 14, 15, 16, or 17 contiguous residues of SEQ ID NO:3). Contiguous residues of SEQ ID NO: 3 include those beginning at any amino acid and ending at any amino acid of SEQ ID NO: 3.

In another embodiment, the purified antibody binds specifically to a 17 residue peptide encoded by the CdtB gene sequence. In particular embodiments, the purified antibody binds specifically to a 17 residue peptide encoded by SEQ ID NO: 2. In various embodiments, the purified antibody binds specifically to a 14, 15, 16, 17, 18, 19, 20, 21, or 22 residue peptide encoded by SEQ ID NO: 2. In various embodiments, the purified antibody binds specifically to a 14, 15, 16, 17, 18, 19, 20, 21, or 22 residue peptide that has at least 80%, 85%, 90%, 95%, 96%, 97%, 98%, 99% or 100% homology to 14, 15, 16, 17, 18, 19, 20, 21, or 22 contiguous residues encoded by SEQ ID NO: 2. In various embodiments, the purified antibody binds specifically to a polypeptide comprising 14, 15, 16, 17, 18, 19, 20, 21, or 22 residues that have at least 80%, 85%, 90%, 95%, 96%, 97%, 98%, 99% or 100% homology to 14, 15, 16, 17, 18, 19, 20, 21, or 22 contiguous residues encoded by SEQ ID NO: 2.

In another embodiment, the purified antibody binds specifically to a peptide encoded by the nucleic acid sequence having the following sequence: CTTGATTATGCAATTACAGGAAATTCAAATAGACAACAAACCTATACTCCA (SEQ ID NO:6), which encodes the 17 amino acid peptide of SEQ ID NO. 3. In another embodiment, the purified antibody binds specifically to a polypeptide comprising a peptide encoded by SEQ ID NO:6.

In another embodiment, the purified antibody binds specifically to CdtB purified from *E. coli* overexpressing a near full-length CdtB ORF. (See Infection and Immunity, December 2000, p. 6535-6541, Vol. 68, No. 12, herein incorporated by reference in its entirety as though fully set forth.)

In another embodiment, the purified antibody binds specifically to CDT and inhibits the binding of CDT to its receptor.

In another embodiment, the purified antibody binds specifically to CDT and achieves at least 25%, 30%, 40%, or 50% neutralization; for example, of $10^4$ infectious units of bacteria or CDT in a 24 hour assay at a concentration of 1 µg antibody per milliliter.

One of skill in the art will be able to produce the antibodies described herein without undue experimentation in light of the disclosure herein, including the examples.

Methods of preparing monoclonal antibodies are known in the art. For example, monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include CDT or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) *Monoclonal Antibodies: Principles and Practice* Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In another embodiment the antibodies to an epitope for CDT as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. *Nature* 321:522-525; Riechmann et al. 1988. *Nature* 332:323-329; Presta. 1992. *Curr. Op. Struct. Biol.* 2:593-596). Humanization can be essentially performed following methods of Winter and co-workers (see, e.g., Jones et al. 1986. *Nature* 321:522-525; Riechmann et al. 1988. *Nature* 332:323-327; and Verhoeyen et al. 1988. *Science* 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In another embodiment the antibodies to an epitope of CDT as described herein or a fragment thereof are human antibodies. Human antibodies can also be produced using various techniques known in the art, including phage display libraries (Hoogenboom and Winter. 1991. *J. Mol. Biol.* 227:381-388; Marks et al. 1991. *J. Mol. Biol.* 222:581-597) or the preparation of human monoclonal antibodies (e.g., Cole et al. 1985. *Monoclonal Antibodies and Cancer Therapy Liss*; Boerner et al. 1991. *J. Immunol.* 147(1):86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. *Bio/Technology* 10:779-783; Lonberg et al. 1994. *Nature* 368:856-859; Morrison. 1994. *Nature* 368:812-13; Fishwild et al. 1996. *Nature Biotechnology* 14:845-51; Neuberger. 1996. *Nature Biotechnology* 14:826; Lonberg and Huszar. 1995. *Intern. Rev. Immunol.* 13:65-93. U.S. Pat. No. 6,719,971 also provides guidance to methods of generating humanized antibodies.

To determine which monoclonal antibodies are CDT inhibitors or CDT neutralizers, the use of a screening assay can be performed. Screening assays are known in the art and can be performed without undue experimentation. (e.g., AbuOun et al., *Cytolethal Distending Toxin (CDT)-Negative Campylobacter jejuni Strains and Anti-CDT Neutralizing Antibodies Are Induced during Human Infection but Not during Colonization in Chickens*. INFECT IMMUN. 2005 May; 73(5): 3053-3062.) For example, monoclonal antibodies may be tested for their capacities to neutralize the in vitro CDT activity from CDT-positive bacterial species (e.g., CDT-positive *C. jejuni* strains). Lysates from CDT-positive *C. jejuni* strains are pretreated with rabbit anti-*C. jejuni* antisera, and the CDT activity is tested for neutralization.

In other embodiments, the agent may be a competitive or noncompetitive inhibitor of a CDT receptor (e.g., a competitive or noncompetitive ligand for a CDT receptor). In various embodiments, the agent is also capable of covalent or noncovalent modification to CDT, its receptor, or a component of an effector in the pathway. In one embodiment, the agent is a CDT receptor antagonist to obviate G2 arrest in the cell (e.g., turns the cell back on).

In another embodiment, the agent may be an agent capable of inhibiting the CDT operon. In one embodiment, the agent may be a regulatory repressor protein capable of binding to the operator and preventing the transcription of the genes on the operon.

Another embodiment of the present invention provides a method of purifying CDT from a biological sample containing CDT, comprising providing an affinity matrix comprising an antibody that binds specifically to CDT bound to a solid support; contacting the biological sample with the affinity matrix, to produce an affinity matrix-CDT complex; separating the affinity matrix-CDT complex from the remainder of the biological sample; and releasing CDT from the affinity matrix.

Another embodiment of the present invention provides a method of treating IBS in a subject in need thereof, comprising providing a composition comprising a CDT inhibitor and/or CDT neutralizer, and administering the composition to the subject to treat the IBS. In one embodiment, the IBS is caused by CDT or resulted from an exposure to CDT; particularly, CDT in the intestines. In various embodiments, the CDT inhibitor and/or CDT neutralizer may be ones as described above.

Another embodiment of the present invention provides a method of preventing IBS or reducing the likelihood of developing IBS in a subject in need thereof, comprising providing a composition comprising a CDT inhibitor and/or CDT neutralizer and administering the composition to the subject to prevent IBS or to reduce the likelihood of developing IBS in the subject. In one embodiment, the IBS is caused by CDT or resulted from an exposure to CDT; particularly, CDT in the intestines. In various embodiments, the CDT inhibitor and/or CDT neutralizer may be a CDT inhibitor and/or CDT neutralizer as described above.

Another embodiment of the present invention provides for a composition to elicit a specific immune response in a subject; for example, a vaccine.

In one embodiment, the composition is useful to prevent IBS, to reduce the likelihood of developing or having IBS, and/or to treat IBS. In one embodiment, the composition comprises a fragment of CDT, CdtA, CdtB, CdtC, CDT mutein, CdtA mutein, CdtB mutein, CdtC mutein, or combinations thereof that will not cause IBS. Such muteins may be used to prevent CDT from causing IBS or to reduce the likelihood of CDT causing IBS. In another embodiment, the composition comprises heat killed, attenuated or inactivated bacteria that contain CDT or the CDT gene. In another embodiment, the composition comprises bacteria with a mutated CDT gene (e.g., a mutated *C. jejuni* strain). In a further embodiment, the composition may further comprise an adjuvant. Examples of adjuvants include but are not limited to inorganic adjuvants (e.g., aluminum salts (aluminum phosphate and aluminum hydroxide)), organic adjuvants, oil-based adjuvants, and virosomes.

One example of a CDT mutein and a CdtB mutein is *Campylobacter jejuni* 81-176 strain with an insertion mutation at CdtB. Thus, in a particular embodiment, the composition to stimulate a specific immune response in a subject comprises the *Campylobacter jejuni* 81-176 strain with an insertion mutation at CdtB.

In another embodiment, the composition comprises a quantity of a bacterial strain that failed to express CDT or a functional CDT due to a mutation at the gene for CDT (e.g., an insertion mutation at the gene for CdtB). In one embodiment, the composition comprises the *Campylobacter jejuni* 81-176 strain that failed to express an active or functional cytolethal distending toxin (CdtB) due to an insertion mutation at the gene for CdtB.

The present invention also provides a method to elicit a specific immune response in a subject. In one embodiment, the method prevents IBS or reduces a subject's likelihood of developing or having IBS. In another embodiment, the method prevents NUD or reduces a subject's likelihood of developing NUD. In one embodiment, the method comprises providing a composition to elicit a specific immune response as described above and administering the composition to the subject.

Administering the composition to the subject may be performed by any method known in the art, and particularly in vaccination therapy (e.g., injection, infusion). In another embodiment, the composition may be administered more than once; for example, "booster shot(s)" may be administered to the subject.

In another embodiment, the present invention provides a method for diagnosing IBS or determining a subject's likelihood of having IBS. In various embodiments, the IBS is post-infections IBS. In one embodiment, the method comprises detecting the presence or absence of CDT or one or more markers indicating a previous exposure to CDT ("CDT marker") in a subject in need thereof and correlating the presence of CDT or one or more CDT markers with a likely presence of IBS or correlating the absence of CDT or one or more CDT markers with a likely absence of IBS. Not all subjects with the presence of CDT or the presence of one or more markers of CDT will have or develop IBS; however, this method provides an indication on a likelihood of whether the subject has IBS or will develop IBS. A determination of a likely presence of IBS may be further correlated and/or confirmed by other diagnostic methods for IBS, or with symptoms of IBS known in the art. Further, a determination of a likely absence of IBS may also be further correlated and/or confirmed by other diagnostics methods for IBS or symptoms of IBS known in the art to rule out IBS.

In another embodiment, the present invention provides a method for diagnosing NUD or determining a subject's likelihood of having NUD. In various embodiments, the NUD is post-infections NUD. In one embodiment, the method comprises detecting the presence or absence of CDT or one or more markers indicating a previous exposure to CDT ("CDT marker") in a subject in need thereof and correlating the presence of CDT or one or more CDT markers with a likely presence of NUD or correlating the absence of CDT or one or more CDT markers with a likely absence of NUD. Not all subjects with the presence of CDT or the presence of one or more markers of CDT will have or develop NUD; however, this method provides an indication on a likelihood of whether the subject has NUD or will develop NUD. A determination of a likely presence of NUD may be further correlated and/or confirmed by other diagnostic methods for NUD, or with symptoms of NUD known the in the art. Further, a determination of a likely absence of NUD may also be further correlated and/or confirmed by other diagnostics methods for NUD or symptoms of IBS known in the art to rule out NUD.

In further embodiments, the above determinations may be used to direct the treatment for the subject. In one embodiment, a subject with the likely presence of IBS or a likelihood of having IBS may be treated with one or more therapies for IBS. In another embodiment, a subject with the likely presence of NUD may be treated with one or more therapies for NUD. One of ordinary skill in the art will be able to select an available treatment for IBS or NUD based on the diagnosis of IBS or NUD. For example, antibiotics such as rifaximin and neomycin can be used to treat IBS or NUD. Particularly, rifaximin can be used to treat diarrhea-predominant IBS, and a rifaximin/neomycin combination can be used to treat constipation-predominant IBS.

In various embodiments, the CDT markers may be antibodies to CDT or a CDT remnant. Methods of detecting CDT or the one or more CDT markers are known in the art and one of ordinary skill in the art will be able to detect CDT without undue experimentation. In one embodiment, the method comprises detecting the presence or absence of a subunit of CDT or one or more markers of a subunit of CDT. In one embodiment, the subunit is CdtA. In another embodiment the subunit of CDT is CdtB. In another embodiment, the subunit of CDT is CdtC. For example, detecting the presence of CDT, or detecting the presence of one or more CDT markers can be done by contacting a biological sample from the subject to one or more substrates capable of detecting the presence of CDT, or detecting the presence of the one or more CDT markers. In various embodiments, the one or more substrates are the antibodies to CDT, CdtA, CdtB, CdtC and fragments thereof as described herein.

In another embodiment, a method of detecting the presence of CDT, CdtA, CdtB, CdtC or a fragment thereof may be performed by providing a nucleic acid probe that hybridizes under stringent conditions to a nucleic acid (e.g., DNA or RNA) that encodes CDT, CdtA, CdtB, CdtC or a fragment thereof to isolate the nucleic acid that encodes CDT, CdtA, CdtB, CdtC or a fragment thereof from a biological sample from a subject. In various embodiments, the nucleic acid probes may be labeled (e.g., fluorescently labeled). The detection may further comprise amplifying the isolated nucleic acid that encodes CDT, CdtA, CdtB, CdtC or a fragment thereof. The presence of the isolated nucleic acid that encodes CDT, CdtA, CdtB, CdtC or a fragment thereof is correlated with a likelihood that the subject was exposed to CDT. As such, the exposure to CDT can indicate that the patient may have IBS.

In alternative embodiments, the results may be further correlated with further tests or symptoms to arrive at a diagnosis of IBS. An absence of the isolated nucleic acid that encodes CDT, CdtA, CdtB, CdtC or a fragment thereof is correlated with a lower likelihood that the subject was exposed to CDT; alternatively, additional tests may be performed on the subject (e.g., on biological samples from the subject) to further correlate or confirm the results to diagnose whether the subject has IBS. For instance, the subject may be tested for the presence or absence of one or more markers of CDT; for example, the presence or absence of anti-CDT antibodies, as discussed herein. The presence or absence of the anti-CDT antibodies can provide further correlation information for a practitioner to reach a diagnosis of whether the subject has IBS.

In various embodiments, the one or more markers of CDT is an antibody that binds specifically to CDT, CdtA, CdtB, CdtC or a fragment thereof. In one particular embodiment, the one or more markers of CDT is an antibody that binds specifically to CdtB or a fragment thereof. The antibody that binds specifically to CDT, CdtA, CdtB, CdtC or a fragment thereof may be one or more of the antibodies described herein. As such, in one embodiment, the method of diagnosing IBS or post-infectious IBS or determining a likely presence or absence of IBS or PI-IBS in a subject in need thereof, comprises detecting the presence or absence of an antibody that binds specifically to CDT, CdtA, CdtB, CdtC or a fragment thereof in the subject; and correlating the presence of the antibody with a likelihood of having IBS or PI-IBS, or correlating the absence of the antibody with a likelihood of not having IBS or PI-IBS. The determination of whether the subject has antibodies against CDT, CdtA, CdtB, CdtC or a fragment thereof is important for the determination of whether the patient may have IBS. In one embodiment, detecting the presence or absence of the antibody is performed on a biological sample obtained from the subject. In another embodiment, detecting the presence or absence of the antibody is performed on a blood sample obtained from the subject.

One of ordinary skill in the art will readily appreciate methods that can be used to detect the presence or absence of an antibody that binds specifically to CDT, CdtA, CdtB, CdtC or a fragment thereof. These methods include but are not limited to immunohistochemistry, flow cytometry, fluorescence in situ hybridization (FISH), radioimmuno assays, and affinity purification.

In one embodiment, detecting the presence or absence of an antibody that binds specifically to CDT, CdtA, CdtB, CdtC or a fragment thereof may be performed by contacting CDT, CdtA, CdtB, CdtC or a fragment thereof to a biological sample obtained from the subject to isolate the antibody that binds specifically to CDT, CdtA, CdtB, CdtC or a fragment thereof, wherein the isolation of the antibody that binds specifically to CDT, CdtA, CdtB, CdtC or a fragment thereof indicates the presence of the antibody and the lack of isolation of the antibody that binds specifically to CDT, CdtA, CdtB, CdtC or a fragment thereof indicates the lack of the antibody. In various embodiments, the fragment of CDT, CdtA, CdtB, CdtC may be the fragments as described herein (e.g., 17 residue peptide of CdtB). As an example, an affinity matrix comprising CDT, CdtA, CdtB, CdtC or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on the CDT, CdtA, CdtB, CdtC or the fragment thereof; the labeled CDT, CdtA, CdtB, CdtC or the fragment thereof can be contacted with a biological sample to allow the antibody (if present) to bind specifically to the labeled CdtA, CdtB, CdtC or fragment thereof. In various embodiments, the labeled CdtA, CdtB, CdtC or fragment thereof can be separated out and analyzed for its binding to the antibody.

In another embodiment, a method of diagnosing IBS, detecting a likelihood of having IBS, or a method of determining the susceptibility of a subject to having IBS, comprises detecting the presence or absence of a host protein with homology to CDT or a subunit of CDT in a subject and correlating the presence of the host protein with a likely presence of IBS or a higher susceptibility to developing IBS or correlating the absence of the host protein with a likely absence of IBS or a lower susceptibility to developing IBS. In certain embodiments, the IBS is PI-IBS. Additional tests may be performed to further correlate or confirm the presence or absence of IBS or PI-IBS or to confirm the higher or lower susceptibility of developing IBS or PI-IBS. In one embodiment, the subunit of CDT is CdtA. In another embodiment the subunit of CDT is CdtB. In another embodiment, the subunit of CDT is CdtC. In one embodiment, the host protein has 100% homology with CDT. In another embodiment, the host protein has at least 80%, 85%, 90%, 95%, 96%, 97%, 98%, or 99% homology with CDT. In one embodiment, the host protein has 100% homology with a subunit of CDT. In another embodiment, the host protein has at least 80%, 85%, 90%, 95%, 96%, 97%, 98%, or 99% homology with the subunit of CDT. In a particular embodiment, the host protein has at least 80%, 85%, 90%, 95%, 96%, 97%, 98%, 99% or 100% homology with CdtB. In other embodiments, the host protein has at least 80%, 85%, 90%, 95%, 96%, 97%, 98%, 99% or 100% homology with 17 contiguous residues of CdtB. In other embodiments, the host protein has at least 80%, 85%, 90%, 95%, 96%, 97%, 98%, 99% or 100% homology with 14, 15, 16, 17, 18, 19, 20, 21 or 22 contiguous residues of CdtB. In various embodiments, the CdtB may be CdtB as disclosed by SEQ ID NO: 1 or SEQ ID NO:5. In still other embodiments, the host protein has at least 80%, 85%, 90%, 95%, 96%, 97%, 98%, 99% or 100% homology with 10, 11, 12, 13, 14, 15, 16, or 17 contiguous residues of SEQ ID NO: 3. Methods of detecting the host protein known in the art and one of ordinary skill in the art will be able to detect the host protein without undue experimentation. For example, detecting the presence of the host protein can be done by contacting a biological sample from the subject to one or more substrates capable of detecting the presence of the host protein. In various embodiments, the one or more substrates are the antibodies that bind specifically to CDT, CdtA, CdtB, CdtC and fragments thereof as described herein.

Examples of biological samples include but are not limited to body fluids, whole blood, plasma, stool, intestinal fluids or aspirate, and stomach fluids or aspirate, serum, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method, the biological sample may be whole blood, blood plasma, blood serum, stool, intestinal fluid or aspirate or stomach fluid or aspirate.

In another embodiment, the present invention provides methods of determining whether a subject has small intestine bacterial overgrowth (SIBO) or whether a subject is susceptible to having SIBO. Without wishing to be bound by any particular theory, the inventors believe that an aspect of CDT is its cause of nerve damage to the gut. The nerve damage may cause impairment in the gut's ability to clear bacteria. The poor clearance of bacteria may result in SIBO, and the subject may develop IBS (e.g., experience symptoms of IBS). Thus, the method comprises detecting the presence or absence of CDT or one or more markers indicating a previous exposure to CDT ("CDT marker") in a subject in need thereof and correlating the presence of CDT or one or more CDT markers with a likely presence of SIBO or a higher susceptibility to having SIBO, or correlating the absence of CDT or one or more CDT markers with a likely absence of SIBO or a lower susceptibility to having SIBO. Not all subjects with the presence of CDT or the presence of one or more markers of CDT will have SIBO, however, this method provides an indication on a likelihood of whether the subject has SIBO or an indication on the susceptibility of the subject to having SIBO. A determination of a likely presence of SIBO or higher susceptibility to having SIBO may be further correlated and/or confirmed by other diagnostic methods for SIBO, or with symptoms of SIBO known the in the art. Further, a determination of a likely absence of SIBO or a lower susceptibility to having SIBO may also be further correlated and/or confirmed by other diagnostic methods for SIBO or symptoms of SIBO known in the art to rule out SIBO.

In another embodiment, the present invention provides a method of predicting a subject's response to antibiotic treatment for IBS, or antibiotic prophylaxis to prevent or reduce the likelihood of having IBS. The method comprises, detecting the presence of CDT, or detecting the presence of one or more CDT markers, and correlating the presence of CDT or the one or more CDT markers with a higher likelihood of responding to the antibiotic treatment, correlating the absence of CDT or the one or more CDT markers with a lower likelihood of responding to the antibiotic treatment. Responding to the antibiotic treatment refers to receiving beneficial results from the antibiotic treatment (e.g., symptoms of IBS are alleviated). Detecting the presence of CDT, or detecting the presence of one or more CDT markers can be done by methods known in the art or as described above. Examples of antibiotics used in the treatment for IBS, or antibiotic prophylaxis to prevent or reduce the likelihood of having IBS include but are not limited to non-absorbable antibiotics (e.g., rifaximin, neomycin).

In various embodiments, the present invention provides pharmaceutical compositions including a pharmaceutically acceptable excipient along with a therapeutically effective amount of a CDT inhibitor, CDT neutralizer, and/or a composition to elicit a specific immune response (CDT vaccine) as described above. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, parenteral, or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective CDT inhibitor, CDT neutralizer, and/or a composition to stimulate a specific immune response (CDT vaccine) as described above can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to kits for practicing the methods of the present invention. Examples of kits include kits for diagnosing IBS or a likelihood of having IBS, preventing IBS, reducing the likelihood of developing IBS, treating IBS, determining the presence of SIBO, determining the subject's susceptibility to having SIBO, predicting a subject's response to antibiotic treatment for IBS, predicting a subject's response to antibiotic prophylaxis to prevent or reduce the likelihood of having IBS, and/or diagnosing NUD or a likelihood of having NUD. The kit is an assemblage of materials or components, including at least one of the anti-CDT antibodies, CDT inhibitors, CDT neutralizers, and/or a composition to elicit a specific immune response (CDT vaccine) as described above.

The exact nature of the components configured in the inventive kit depends on its intended purpose. For example, various embodiments are configured for the purposes of preventing IBS, reducing the likelihood of developing IBS, treating IBS, determining the presence of SIBO, determining the subject's susceptibility to having SIBO, predicting a subject's response to antibiotic treatment for IBS, predicting a subject's response to antibiotic prophylaxis to prevent or reduce the likelihood of having IBS, and/or diagnosing NUD or a likelihood of having NUD. In one embodiment, the kit is configured particularly for mammalian subjects. In another embodiment, the kit is configured particularly for human subjects. In further embodiments, the kit is configured for veterinary applications, for subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to prevent IBS, reduce the likelihood of developing IBS, treat IBS, determine the presence of SIBO, determine the subject's susceptibility to having SIBO, predict a subject's response to antibiotic treatment for IBS, predict a subject's response to antibiotic prophylaxis to prevent or reduce the likelihood of having IBS, and/or diagnose NUD or a likelihood of having NUD. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in IBS treatment or antibody treatment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a CDT inhibitor and/or CDT neutralizer, or a composition to elicit a specific immune response, an antibody to detect CDT or a fragment thereof as described above. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Adult male Sprague-Dawley rats were gavaged with either *Campylobacter jejuni* 81-176 (C+) or a CDT-knockout (CDT−) strain of *Campylobacter*. The CDT− strain was a *Campylobacter jejuni* 81-176 strain that failed to express cytolethal distending toxin (CdtB) due to an insertion mutation at the gene for CdtB. After gavage, rats were followed with daily stool culture for *Campylobacter* until 2 consecutive negative cultures were seen. Once cleared of colonization, rats were housed in identical conditions for 3 months (post-infectious). At the end of 3 months, fresh stool was collected by anal stimulation and used to evaluate both the appearance (on a modified Bristol score) and stool weight before and after being placed in an oven overnight. The percentage dry stool weights were calculated. Both groups were compared for stool dry weight, variability in dry weight by day and stool consistency and variability.

Example 2

Both groups of rats (C+ and CDT−) demonstrated equal colonization of the rat as evidenced by positive and prolonged detection in stool after gavage. Three months after loss of *Campylobacter*, the average stool dry weights for all three days were similar between groups (Table 1). However, the variability in stool form and weight was significantly different between groups. The rats exposed to wild type *Campylobacter* had a substantial variability in stool weight and also had altered stool consistency. The rats exposed to CDT-*Campylobacter* had stool form and variability identical to that of healthy control rats.

TABLE 1

Comparison of stool percentage dry weights and consistency

|  | Control | C+ | CDT− |
|---|---|---|---|
| Average % of stool dry weight | 63.7 ± 3.2 | 60.1 ± 6.8 | 61.0 ± 6.3 |
| Daily variability of Dry Weight | 4.9 ± 3.8 | 8.4 ± 6.4 | 4.9 ± 5.5* |
| Average Stool Consistency (Based on Bristol Stool Scale) | 1.0 | 1.5 ± 0.4 | 1.2 ± 0.3** |
| Daily Variability of Stool Consistency | N/A | 0.51 ± 0.38 | 0.30 ± 0.34*** |

*P value = 0.004 when compared to C+
**P value = 0.000025 when compared to C+
***P value = 0.006 when compared to C+

Example 3

Male Sprague-Dawley rats were gavaged with $10^8$ cfu of either wildtype or cdtB mutant *C. jejuni* 81-176. Rats were evaluated at 2 and 4 days post-infection, and at 3 months after infection had cleared (including rats with or without long term sequelae of chronic altered bowel function in the post-infectious period). Control rats were gavaged with vehicle alone. At time of euthanasia, laparotomy was performed and ileal tissue (5 cm proximal to ileocecal valve) was stained with two different antibodies against CdtB: One was raised against CdtB purified from *E. coli* overexpressing a near full-length cdtB ORF; the second antibody was derived from rabbits inoculated with an 18 residue peptide (CLDYAITGNSRQQTYTP (SEQ ID NO:4)), which consist of a cysteine added on the N-terminus of SEQ ID NO:3 for conjugation. Pre-immune rabbit serum was used as a control.

Example 4

During acute infection, CdtB staining was prominent at the epithelial surface of the mucosa. Interestingly, both types of anti-CdtB specific antibodies stained intestinal neural elements, including ICC and myenteric ganglia. This widespread staining of neural elements was seen not only in rats exposed to wildtype *C. jejuni*, but also in rats exposed to cdtB mutants and rats never exposed to *C. jejuni*. Exposure to rabbit pre-immune sera produced no obvious staining of any rat ileal tissue.

Example 5

Plasmids and Construction of Insertion-Deletion Mutants

The *Campylobacter* aphA-3 cassette (Labigne-Roussel et al., 1988. Gene disruption and replacement as a feasible approach for mutagenesis of *Campylobacter jejuni*. J. BACTERIOL. 170:1704-1708), which confers kanamycin resistance, was amplified by PCR from plasmid pRY107. The CdtB ORF sequence was cleaved in the middle by a restriction enzyme and the aphA-3 cassette (Yao et al., 1993. Construction of new Campylobacter cloning vectors and a new mutational cat cassette. GENE 130:127-130) was cloned into that site to disrupt the cdtB sequence and prevent the expression of a functional CdtB. This plasmid was then electroporated into strain 81-176. Double crossover homologous recombinants, which were kanamycin resistant, were identified and underwent further PCR analysis to verify disruption of the CdtB ORF.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of detecting the presence or absence of an antibody capable of binding specifically to cytolethal distending toxin (CDT), CdtA, CdtB, CdtC, or a fragment thereof, comprising:
   detecting the presence or absence of an antibody capable of binding specifically to cytolethal distending toxin (CDT), CdtA, CdtB, CdtC, or a fragment thereof by using CDT, CdtA, CdtB, CdtC, or a fragment thereof to assay a biological sample obtained from a subject having a small intestinal bacterial overgrowth (SIBO) symptom.

2. The method of claim 1, comprising detecting the presence or absence of the antibody capable of binding specifically to CdtB or a fragment thereof by contacting CdtB or the fragment thereof to the biological sample obtained from the subject.

3. The method of claim 1, comprising detecting the presence or absence of the antibody capable of binding specifically to CdtB of *Campylobacter jejuni* or a fragment thereof by contacting CdtB of *Campylobacter jejuni* or the fragment thereof to the biological sample obtained from the subject.

4. The method of claim 3, wherein the CdtB of *Campylobacter jejuni* has an amino acid sequence at least 80% identical to SEQ ID NO:5.

5. The method of claim 3, wherein CdtB of *Campylobacter jejuni* has an amino acid sequence as set forth in SEQ ID NO:5.

6. The method of claim 3, wherein the antibody is capable of binding specifically to an epitope on 5 to 22 contiguous residues of SEQ ID NO:5.

7. The method of claim 6, wherein the epitope is on 17 contiguous residues as disclosed by SEQ ID NO:3.

8. The method of claim 1, wherein the antibody is capable of binding specifically to an epitope on SEQ ID NO:4.

9. The method of claim 1, comprising detecting the presence or absence of the antibody capable of binding specifically to CdtB of *Campylobacter coli* or a fragment thereof by contacting CdtB of *Campylobacter coli* or the fragment thereof to the biological sample obtained from the subject.

10. The method of claim 9, wherein the CdtB of *Campylobacter coli* has an amino acid sequence at least 80% identical to SEQ ID NO:1.

11. The method of claim 9, wherein the CdtB of *Campylobacter coli* has an amino acid sequence as set forth in SEQ ID NO:1.

12. The method of claim 1, wherein the CdtB is CdtB of *Escherichia coli*, *Salmonella*, *Shigella* or *Clostridium difficile*.

13. The method of claim 1, wherein assaying comprises contacting CDT, CdtA, CdtB, CdtC or a fragment thereof with the biological sample to detect the presence or absence of the antibody.

14. The method of claim 1, wherein assaying comprises using immunohistochemistry.

15. The method of claim 1, wherein assaying comprises using flow cytometry.

16. The method of claim 1, wherein assaying comprises using fluorescence in situ hybridization (FISH).

17. The method of claim 1, wherein assaying comprises using a radioimmuno assay.

18. The method of claim 1, wherein assaying comprises using affinity purification.

19. The method of claim 1, wherein the biological sample is whole blood, plasma or serum.

20. The method of claim 1, further comprising directing the subject to a SIBO treatment when the presence of the antibody capable of binding specifically to CDT, CdtA, CdtB, CdtC, or the fragment thereof is detected.

21. The method of claim 1, wherein the subject having the SIBO symptom is a human subject.

22. A method of detecting the presence or absence of an antibody capable of binding specifically to cytolethal distending toxin B (CdtB) of *Campylobacter jejuni* or a fragment thereof, comprising:

detecting the presence or absence of an antibody capable of binding specifically to cytolethal distending toxin B (CdtB) of *Campylobacter jejuni* or a fragment thereof by contacting CdtB of *Campylobacter jejuni* or a fragment thereof with whole blood, plasma or serum obtained from a human subject having a small intestinal bacterial overgrowth (SIBO) symptom, in an assay.

23. The method of claim 22, further comprising directing the subject to a SIBO treatment when the presence of the antibody capable of binding specifically CdtB or the fragment thereof is detected.

\* \* \* \* \*